US00PP35828P3

(12) United States Plant Patent
Rodriguez Armenta et al.

(10) Patent No.: US PP35,828 P3
(45) Date of Patent: May 28, 2024

(54) BLUEBERRY PLANT NAMED 'FCM17-132'

(50) Latin Name: *Vaccinium corymbosum*
Varietal Denomination: FCM17-132

(71) Applicant: Fall Creek Farm and Nursery, Inc., Lowell, OR (US)

(72) Inventors: Hilda Patricia Rodriguez Armenta, Jalisco (MX); Peter Stefan Boches, Hilo, HI (US)

(73) Assignee: FALL CREEK FARM AND NURSERY, INC., Lowell, OR (US)

( * ) Notice: Subject to any disclaimer, the term of this patent is extended or adjusted under 35 U.S.C. 154(b) by 108 days.

(21) Appl. No.: 18/108,134

(22) Filed: Feb. 10, 2023

(65) Prior Publication Data

US 2023/0270032 P1 Aug. 24, 2023

Related U.S. Application Data

(60) Provisional application No. 63/310,179, filed on Feb. 15, 2022.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

PP24,606 P3 7/2014 Brazelton et al.
PP29,287 P3 5/2018 Brazelton et al.

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

The new blueberry plant variety 'FCM17-132' is provided. 'FCM17-132' is a commercial variety intended for the hand harvest fresh fruit market. The variety is produced from a cross of 'FCM12-096' (female parent, not patented) and 'FL01-06' (male parent, not patented). 'FCM17-132' displays high vigor and exhibits round to sprawling plant shape.

6 Drawing Sheets

Latin name of the genus and species:
Genus—*Vaccinium.*
Species—*corymbosum.*
Variety denomination: The new blueberry plant claimed is of the variety denominated 'FCM17-132'.

STATEMENT REGARDING FEDERALLY-SPONSORED RESEARCH AND DEVELOPMENT

None.

BACKGROUND OF THE INVENTION

The present invention relates to the discovery of a new and distinct cultivar of highbush blueberry (*Vaccinium corymbosum*) plant, referred to as 'FCM17-132' as herein described and illustrated. The new blueberry plant variety 'FCM17-132' is a commercial variety intended for the hand harvest fresh fruit market.

Pedigree and History: The new blueberry plants originated from a cross of 'FCM12-096' female parent (not patented) and 'FL01-06' male parent (unpatented). The new blueberry 'FCM17-132' was initially crossed in 2014 in Tala, Jalisco, Mexico, and planted in 2015 in a seedling plot.

'FCM17-132' has been found to undergo asexual propagation by soft wood cuttings in Tala, Jalisco, Mexico and by in vitro propagation in Oregon. Asexual propagation techniques in Tala, Jalisco, Mexico and Oregon, such as soft wood cuttings and in vitro propagation, have shown that the characteristics of the new variety are homogenous, stable, and strictly transmissible by such asexual propagation from one generation to another. Accordingly, the new variety undergoes asexual propagation in a true-to-type manner.

SUMMARY OF THE INVENTION

The following characteristics of the new cultivar have been repeatedly observed and are determined to be the unique characteristics of the new blueberry plant variety 'FCM17-132':

(a) displays high vigor,
(b) exhibits round to sprawling plant shape, and
(c) provides large fruit.

The new variety of the present invention can readily be distinguished from its ancestors. More specifically, the 'FCM12-096' variety (i.e., the seed parent) is a sprawling low vigor plant, whereas the new variety is a high vigor plant with sprawling to round shape. The 'FL01-06' variety (i.e., the pollen parent) displays medium vigor, exhibits an upright habit, and produces fruit which has medium firmness and very high acidity, whereas the new variety displays high vigor, exhibits a sprawling to round habit, and produces fruit which has high firmness and medium acidity.

The new variety can also be distinguished from other similar varieties that are commercially available. For instance, the new variety of the present invention can readily be distinguished from the 'Biloxi' variety (not patented), as the new cultivar displays larger sized fruit, as compared to plants of the 'Biloxi' variety.

The new variety has not yet been offered for sale or sold as of February 2022.

BRIEF DESCRIPTION OF THE DRAWINGS

The accompanying photographic illustration shows typical specimens in full color of the foliage and fruit of plants of the new variety 'FCM17-132'. The age of the plants illustrated was approximately three to four years old. The colors are as nearly true as is reasonably possible in a color representation of this type. The colors in the photographs are as close as possible with the photographic and printing technology utilized. The color values cited in the detailed botanical description accurately describe the colors of the new blueberry.

DETAILED BOTANICAL DESCRIPTION

Figure 1:
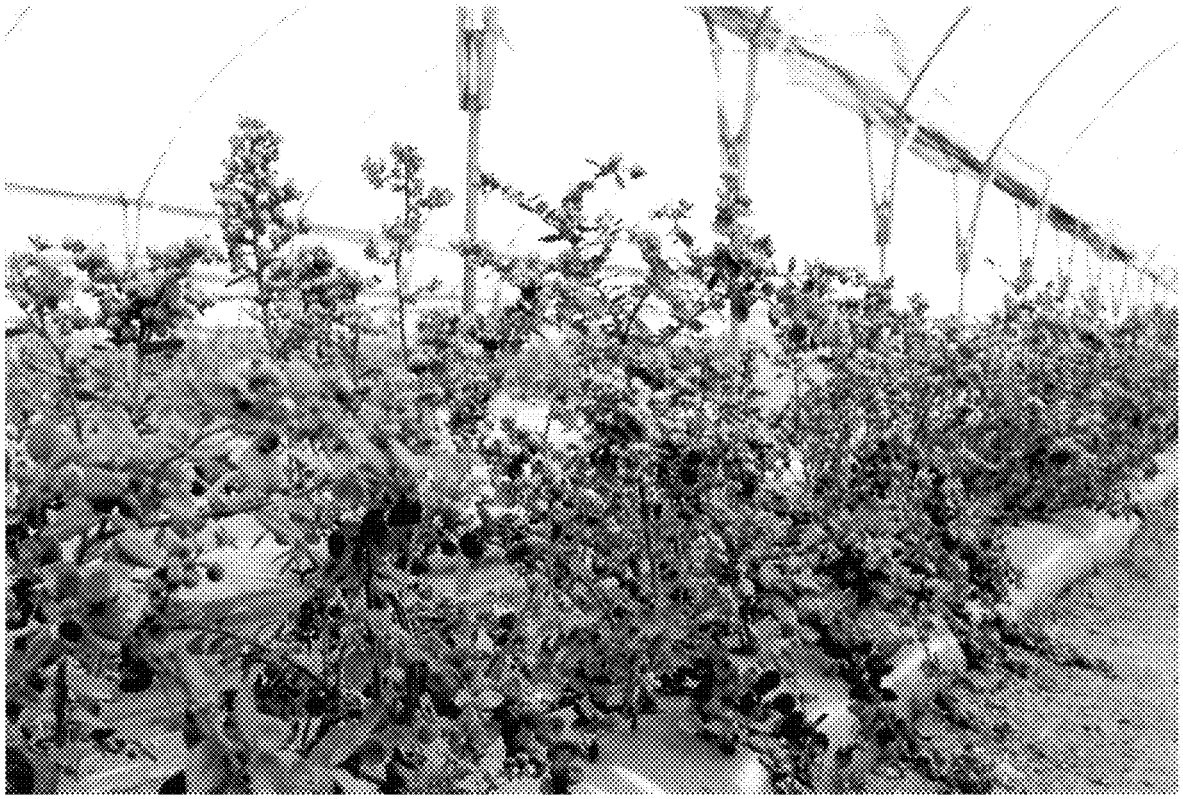
FIG. 1 depicts the new variety's round to sprawling growth habit. The plants were grown in Tala, Jalisco, Mexico and photographed on Jan. 17, 2019.
Figure 2:
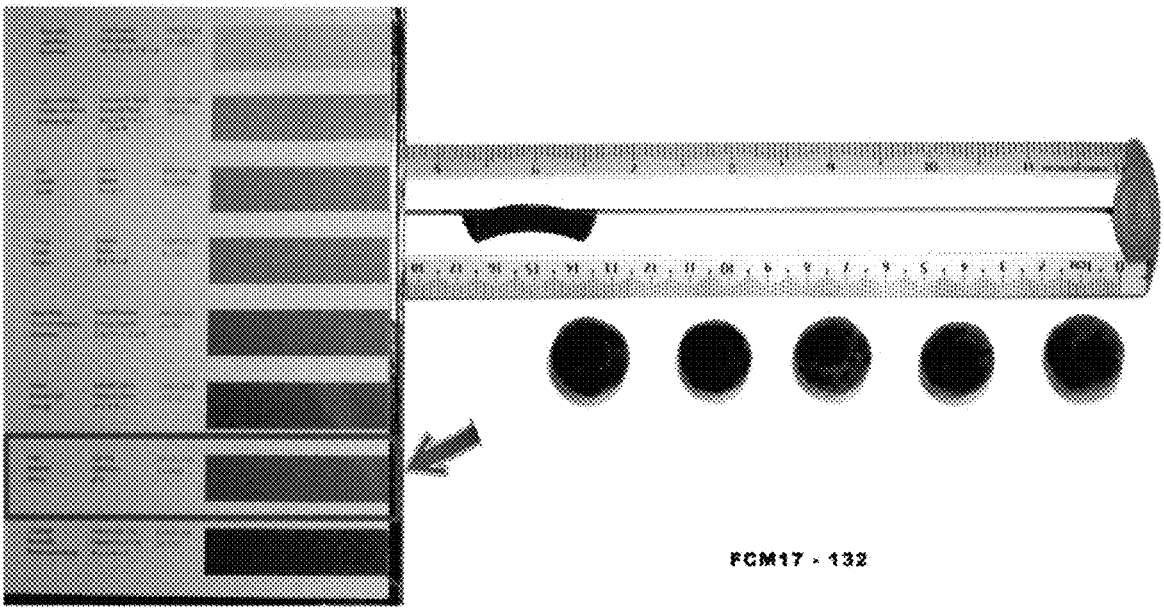
FIG. 2 depicts fruit of the new variety with scale and Pantone colors. The fruit was grown in Tala, Jalisco, Mexico and photographed on Nov. 13, 2018.
Figure 3:
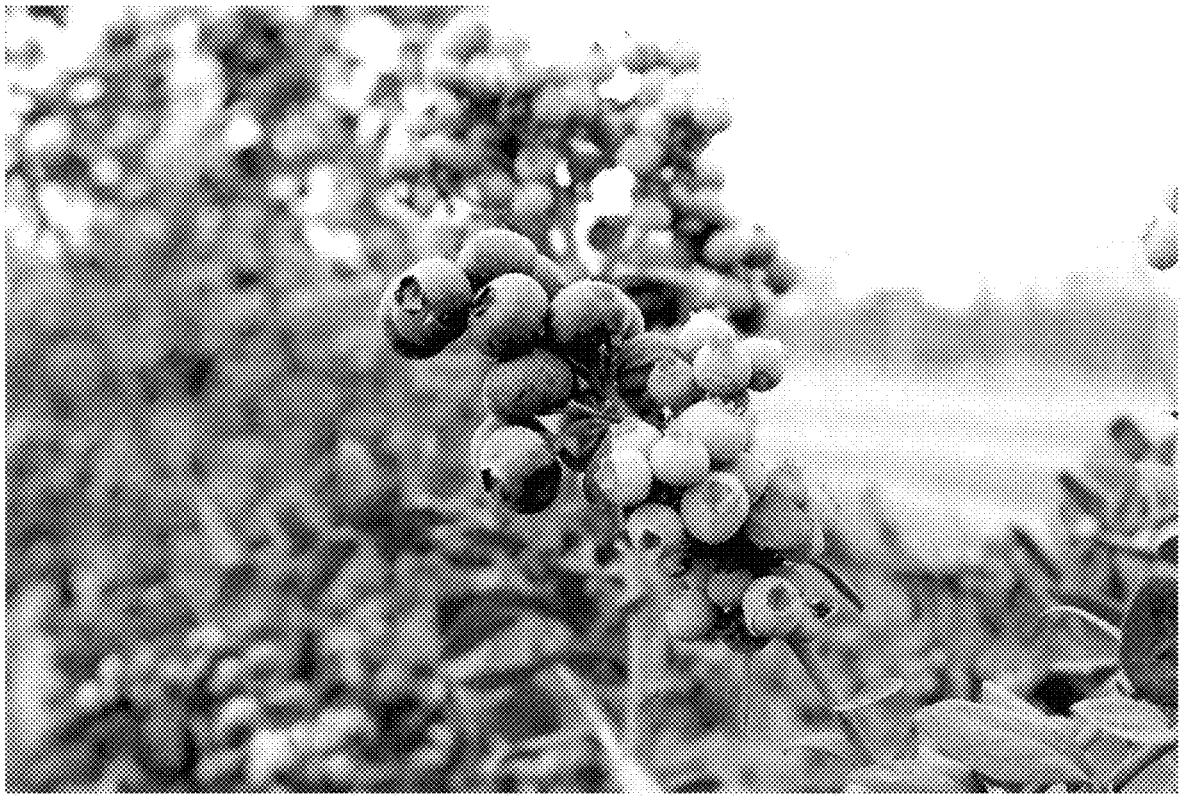
FIG. 3 depicts a cluster with some ripe and unripe fruit on the plant of the new variety. The fruit and plant were grown in Tala, Jalisco, Mexico and photographed on Jan. 17, 2019.
Figure 4:
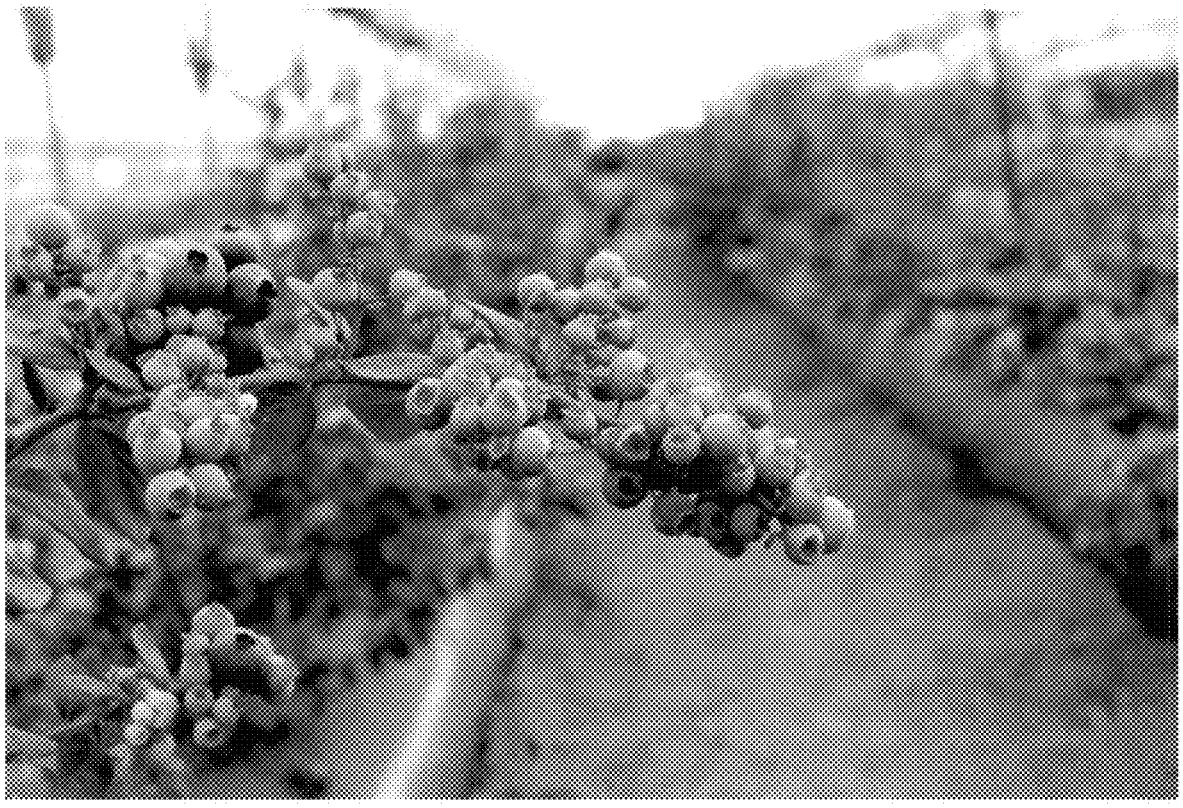
FIG. 4 depicts an unripe fruit cluster on the plant of the new variety 'FCM17-132'. The fruit and plant were grown in Tala, Jalisco, Mexico and photographed on Jan. 17, 2019.
Figure 5:
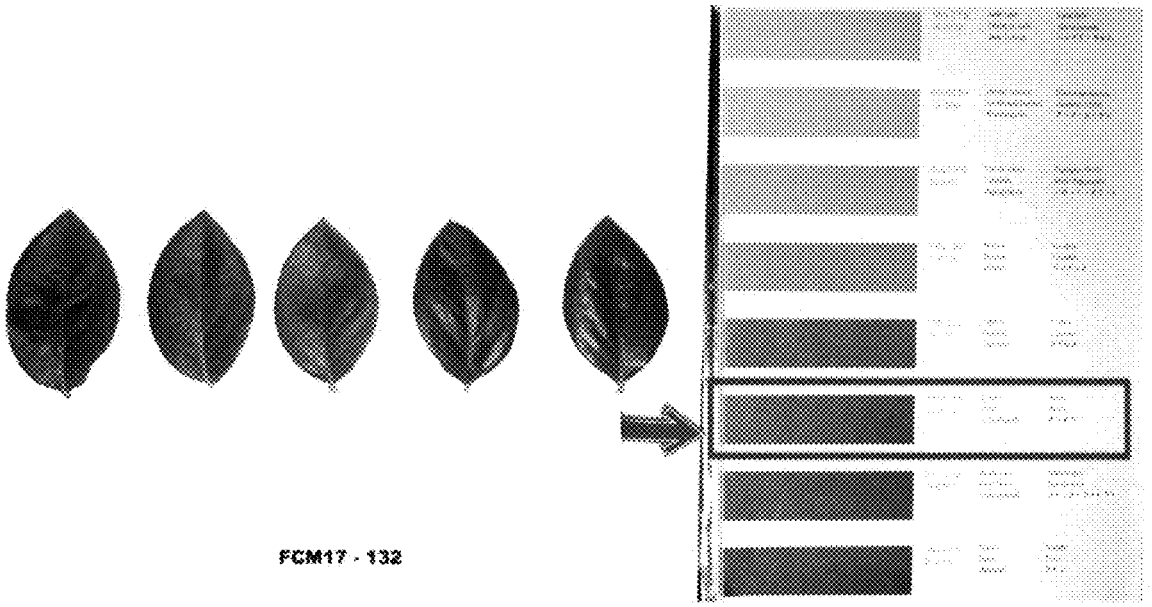
FIG. 5 depicts mature foliage of the new variety with scale and Pantone colors. The plants were grown in Tala, Jalisco, Mexico and photographed on Nov. 13, 2018.
Figure 6:
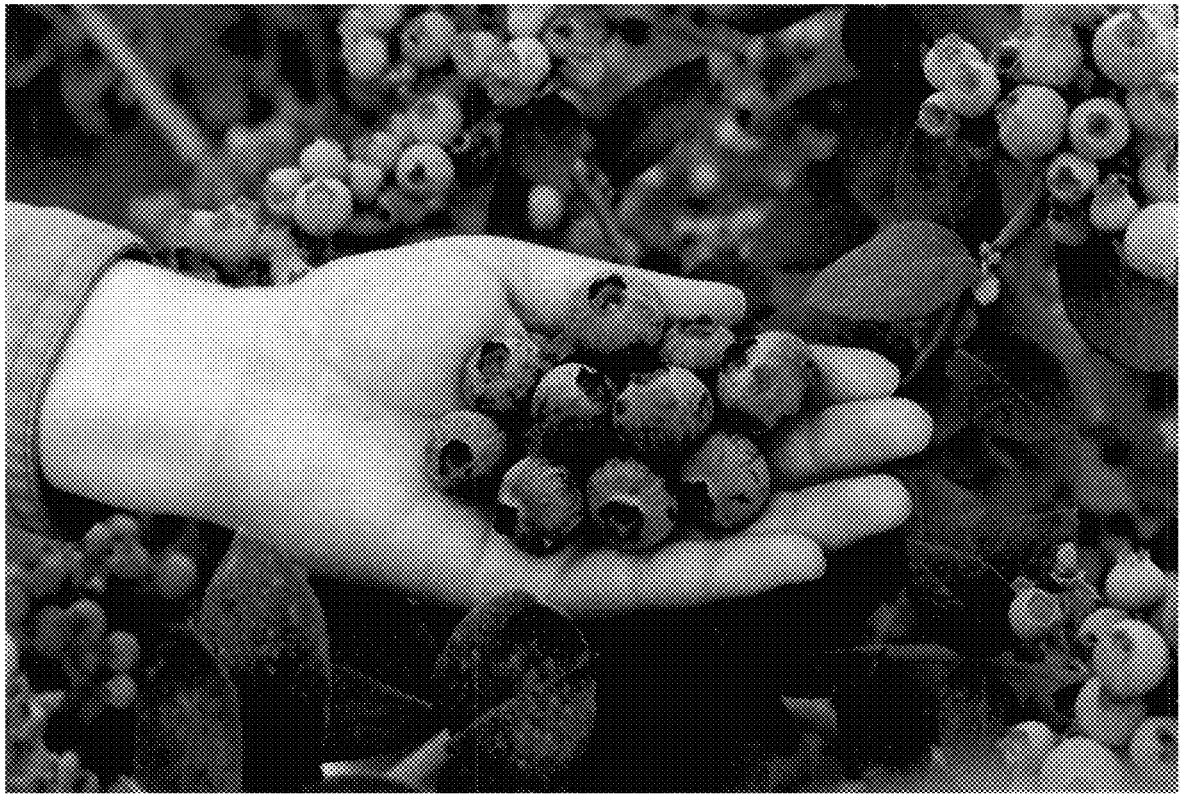
FIG. 6 depicts ripe fruit of the new variety demonstrating the size and color. The fruit was grown in Tala, Jalisco, Mexico and photographed on Jan. 17, 2019.

The following detailed description sets forth the distinctive characteristics of 'FCM17-132'. The data which defines these characteristics was collected from asexual reproductions of the original selection. Dimensions, sizes, colors, and other characteristics are approximations and averages set forth as accurately as possible. The plant history was taken on plants approximately 3 years of age, and the descriptions relate to plants grown in the field in Tala, Jalisco, Mexico. Descriptions of fruit characteristics were made on fruit grown in Tala, Jalisco, Mexico. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

The new blueberry plant variety 'FCM17-132' has not been observed under all possible environmental conditions. The phenotype may vary somewhat with variations in environment and cultural practices such as temperature and light intensity without, however, any variance in genotype.

VARIETY

Classification:

*Family*.—Ericaceae.

*Genus*.—*Vaccinium*.

*Species*.—*corymbosum*.

*Common name*.—Highbush Blueberry.

Parentage:

*Female parent*.—'FCM12-096' (unpatented).

*Male parent*.—'FL01-06' (unpatented).

Market class: Commercial blueberry variety intended for the hand harvest fresh market.

PLANT

General:

*Plant height*.—149 cm.

*Plant width*.—167 cm.

*Growth habit*.—Round to sprawling.

*Growth*.—High vigor.

*Productivity*.—High.

*Cold hardiness*.—No information available for cold damage.

*Cold tolerance*.—Very low resistance to low temperatures.

*Chilling requirement*.—Zero.

*Leafing*.—Medium.

*Twigginess*.—High.

*Tolerance to disease*.—No information available.

*Resistance/susceptibility to root rot* (*Phytopthora cinnamomii*).—No information available.

*Resistance/susceptibility to stem blight* (*Botryosphaeria sp.*).—No information available.

*Resistance/susceptibility to Phomopsis twig blight* (*Phomopsis vaccinii*).—No information available.

*Resistance/susceptibility to Botrytis* (*Botrytis cinerea*).—No information available.

*Resistance/susceptibility to leaf spot* (*Septoria spp.*).—No information available.

*Resistance/susceptibility to leaf rust* (*Naohidemyces vaccinii*).—Low rust incidence.

*Resistance/susceptibility to bud mites* (*Acalatus vaccinii*).—No information available.

STEM

General:

*Suckering tendency*.—High.

*Mature cane color*.—Pantone Cork 16-1422.

*Mature cane length*.—70.8 cm.

*Mature cane width*.—3.618 cm at 6 inches from the crown.

*Bark texture*.—Rough.

*Fall color on new shoots*.—Pantone Green Oasis 15-0538.

*Surface texture of new wood*.—Smooth.

*Internode length on strong, new shoots*.—15.608 mm.

*Fruiting wood*.—31.2 cm in length.

FOLIAGE

General:

*Time of beginning of leaf bud burst*.—Under testing conditions, plants do not enter dormancy.

*Leaf color* (*top side*).—Pantone Chive 19-0323.

*Leaf color* (*under side*).—Pantone Epsam 17-0324.

*Leaf arrangement*.—Alternate and distichous.

*Leaf shape*.—Ovate.

*Leaf margins*.—Entire in young leaves and serrate on mature leaves.

*Undulation of margin*.—Flat.

*Leaf venation*.—Anastomosing.

*Leaf apices*.—Acute.
*Leaf bases*.—Rounded.
*Leaf length*.—62.57 mm.
*Leaf width*.—39.226 mm.
*Leaf length/width ratio*.—1.59.
*Leaf nectarines*.—Absent.
*Pubescence of upper side*.—Absent on young leaves, hispid on mature leaves.
*Pubescence of lower side*.—Absent on young leaves, hispid on mature leaves.
*Cross sectional profile*.—Undulate.
*Longitudinal profile*.—Entire.
*Attitude*.—Ascending.
*Fall foliage leaf color* (*top side*).—Pantone Chive 19-0323.

Petioles:
*Length*.—4.438 mm.
*Width*.—2.464 mm.
*Color*.—Pantone Sweet Pea 15-0531.
*Surface texture*.—Soft.

FLOWERS

General:
*Time of beginning of flowering*.—Mid August, or mid October. Around 150 days after pruning.
*Time of* 50% *anthesis*.—December or around 225 days after pruning.
*Flower shape*.—Cupuliform.
*Flower bud density*.—High.
*Flower fragrance*.—Mild fragrance, sweet.
*Immature flower color*.—Pantone Frozen Dew 13-0513.
*Pollen staining*.—Not observed.

Corolla:
*Color*.—Pantone Frozen Dew 13-0513.
*Length*.—9.16 mm.
*Width*.—8.448 mm.
*Aperture width*.—4.188 mm.
*Anthocyanin coloration of corolla*.—Low.
*Corolla ridges*.—Distinct.
*Protrusion of stigma*.—Stigma is shorter than the corolla.

Inflorescence:
*Length*.—61.496 mm.
*Diameter*.—37.88 mm.
*Length of peduncle*.—52.962 mm.
*Surface texture of peduncle*.—Rough.
*Color of peduncle*.—Pantone Spinach Green 16-0439.
*Length of pedicel*.—18.13 mm.
*Surface texture of pedicel*.—Rough.
*Color of pedicel*.—Pantone Spinach Green 16-0439.
*Number of flowers per cluster*.—Average 9.6.
*Flower cluster density*.—High.

Calyx (with sepals):
*Diameter*.—8.366 mm.
*Color* (*sepals*).—Pantone Lettuce Green 13-0324.
*Surface texture*.—Soft.

Stamen:
*Length*.—4.428 mm.
*Number per flower*.—Average 10.
*Filament color*.—Pantone Adobe 17-1340.

Anther:
*Length*.—2.208 mm.
*Number*.—2 per filament.
*Color*.—Pantone Inca Gold 17-1048.

Pollen:
*Abundance*.—Medium.
*Color*.—Pantone Cornsilk 13-0932.
*Self-compatibility*.—High.

Pistil:
*Length*.—8.284 mm.
*Ovary color* (*exterior*).—Pantone Green Olive 18-0527.
*Style length*.—4.138 mm.

FRUIT

General:
*Time of fruit ripening*.—End of fall to summer. From October to end of February when pruned in March, and from December to end of May when pruned in June.
*Time of* 50% *maturity*.—Mid November and end of December.
*Fruit development period*.—70 days average.
*Mean harvest date*.—Mid December and mid-March.
*Mean date last pick*.—End of February and end of May.
*Plant fruiting type*.—Only from one year old shoots.
*Cluster density*.—9.6 average berries per cluster.
*Unripe fruit color*.—Pantone Mellow Green 12-0426.
*Ripe berry color*.—Pantone Charcoal Gray 18-0601.
*Berry skin color after polishing*.—Pantone Shale 19-3930.
*Berry surface wax abundance*.—Medium.
*Berry flesh color*.—Pantone Lily Green 13-0317.
*Berry weight*.—2.58 grams.
*Berry height from calyx to scar*.—16.93 mm.
*Berry diameter*.—21.094 mm.
*Calyx aperture*.—6.808 mm.
*Calyx depth*.—2.846 mm.
*Pedicel length*.—18.13 mm.
*Pedicel surface texture*.—Rough.
*Berry detachment force*.—Medium.
*Berry shape*.—Slight oblate.
*Fruit stem scar*.—Small and dry.
*Sweetness when ripe*.—Medium.
*Firmness when ripe*.—High.
*Acidity when ripe*.—Medium.
*Storage quality*.—Good, 35 days at 6 C degrees.
*Suitability for mechanical harvesting*.—No information available.
*Self-fruitfulness*.—High, under controlled manual crosses a fruit set of 66% was obtained when the flowers were pollinated with their own pollen.
*Uses*.—Fresh.

SEED

General:
*Seed abundance in fruit*.—Medium, around 20 seeds per berry.
*Seed color*.—Pantone Hazel 17-1143.
*Seed dry weight*.—0.068 grams per 100 seeds
*Seed length*.—2.014 mm. .

COMPARISON BETWEEN COMMERCIAL CULTIVARS

TABLE 1

Comparison Table

| Denomination of similar variety | Characteristic for comparison | State of expression of similar variety | State of expression of candidate variety 'FCM17-132' |
|---|---|---|---|
| 'Biloxi' (unpatented) | Fruit: size | Small to medium | Large |
| 'Biloxi' (unpatented) | Plant: shape | Round | Semi sprawling |
| 'Ventura' (U.S. Plant Pat. No. 24,606) | Fruit: color | Light blue | Medium dark |

TABLE 1-continued

Comparison Table

| Denomination of similar variety | Characteristic for comparison | State of expression of similar variety | State of expression of candidate variety 'FCM17-132' |
|---|---|---|---|
| 'FCM12-087' (U.S. Plant Pat. No. 29,287) | Plant: vigor | Medium | High |
| 'FCM12-087' (U.S. Plant Pat. No. 29,287) | Crop: production time | Very late | Late |

We claim:

1. A new and distinct variety of blueberry plant named 'FCM17-132', substantially as illustrated and described herein.

* * * * *